United States Patent
Tsuyuki et al.

(10) Patent No.: US 9,030,543 B2
(45) Date of Patent: May 12, 2015

(54) ENDOSCOPE SYSTEM

(71) Applicants: Olympus Medical Systems Corp., Tokyo (JP); Olympus Corporation, Tokyo (JP)

(72) Inventors: Hiroshi Tsuyuki, Tokyo (JP); Takeshi Suga, Tokyo (JP); Masao Sambongi, Tokyo (JP)

(73) Assignees: Olympus Medical Systems Corp., Tokyo (JP); Olympus Corporation, Tokyo (JP)

( * ) Notice: Subject to any disclaimer, the term of this patent is extended or adjusted under 35 U.S.C. 154(b) by 0 days.

(21) Appl. No.: 14/138,083

(22) Filed: Dec. 22, 2013

(65) Prior Publication Data

US 2014/0176692 A1    Jun. 26, 2014

Related U.S. Application Data

(63) Continuation of application No. PCT/JP2013/065924, filed on Jun. 10, 2013.

(30) Foreign Application Priority Data

Jun. 28, 2012    (JP) ................. 2012-145198

(51) Int. Cl.
*H04N 9/47*    (2006.01)
*H04N 7/18*    (2006.01)
(Continued)

(52) U.S. Cl.
CPC ............ *H04N 5/265* (2013.01); *G02B 23/2423* (2013.01); *G02B 23/2469* (2013.01); *G02B 23/2484* (2013.01); *A61B 1/00009* (2013.01); *A61B 1/00096* (2013.01);
(Continued)

(58) Field of Classification Search
None
See application file for complete search history.

(56) References Cited

U.S. PATENT DOCUMENTS 4,676,593 A    6/1987    Adachi et al.
5,976,071 A *  11/1999   Sekiya ..................... 600/111
(Continued)

FOREIGN PATENT DOCUMENTS

JP    59-164022    11/1984
JP    2002-010126    1/2002
(Continued)

OTHER PUBLICATIONS

International Search Report, dated Aug. 30, 2013, issued in corresponding International Application No. PCT/JP2013/065924.

*Primary Examiner* — Joseph Ustaris
*Assistant Examiner* — Rebecca Volentine
(74) *Attorney, Agent, or Firm* — Kenyon & Kenyon LLP

(57) ABSTRACT

An image with an expanded depth of field is more effectively acquired while reducing the manufacturing cost, without enlarging the apparatus.
Provided is an endoscope system including: an objective optical system that is provided at an insertion portion tip and that acquires a subject image; an optical path division means for dividing the subject image into two optical images with different focuses; an imaging element that forms the two optical images with different focuses at the same time to acquire two images; an image correction means that corrects the two images acquired by the imaging element so that differences other than the focuses become substantially the same; and an image combination processing unit that selects an image with a relatively high contrast in predetermined corresponding areas between the two images corrected by the image correction means to generate a combined image.

10 Claims, 13 Drawing Sheets

(51) Int. Cl.

| | | |
|---|---|---|
| *A62B 1/04* | (2006.01) | |
| *A61B 1/04* | (2006.01) | |
| *A61B 1/06* | (2006.01) | |
| *H04N 5/265* | (2006.01) | |
| *G02B 23/24* | (2006.01) | |
| *A61B 1/00* | (2006.01) | |
| *H04N 5/217* | (2011.01) | |
| *H04N 5/225* | (2006.01) | |
| *H04N 9/07* | (2006.01) | |
| *H04N 5/232* | (2006.01) | |
| *H04N 5/235* | (2006.01) | |
| *A61B 1/05* | (2006.01) | |

(52) U.S. Cl.
CPC .............. *A61B 1/00188* (2013.01); *A61B 1/05* (2013.01); *H04N 5/2173* (2013.01); *H04N 5/2256* (2013.01); *H04N 7/183* (2013.01); *H04N 9/07* (2013.01); *H04N 5/23212* (2013.01); *H04N 5/23229* (2013.01); *H04N 5/2354* (2013.01)

(56) References Cited

U.S. PATENT DOCUMENTS

| | | | |
|---|---|---|---|
| 8,675,290 B2 * | 3/2014 | Rohaly et al. | 359/740 |
| 2010/0079587 A1 * | 4/2010 | Yoshida | 348/68 |
| 2010/0166293 A1 * | 7/2010 | Sugita et al. | 382/154 |
| 2011/0157350 A1 * | 6/2011 | Yamamoto | 348/79 |
| 2013/0041216 A1 * | 2/2013 | McDowall | 600/109 |
| 2013/0041221 A1 * | 2/2013 | McDowall et al. | 600/111 |

FOREIGN PATENT DOCUMENTS

| | | |
|---|---|---|
| JP | 2003-078802 | 3/2003 |
| JP | 2004-154258 | 6/2004 |
| JP | 2004-313523 | 11/2004 |
| JP | 2009-206831 | 9/2009 |
| JP | 2011-062378 | 3/2011 |
| JP | 2012-095828 | 5/2012 |

\* cited by examiner

FIG. 7A

| EXAMPLES | 2.4≦Fno. /Pix≦4.28 | Pix (μm) | Fno. | k1 | k2 |
|---|---|---|---|---|---|
| EXAMPLE 1 | 4.28 | 1.7 | 7.27 | 3.0 | 0.95 |
| EXAMPLE 2 | 2.40 | 1.45 | 3.48 | 2.0 | 0.80 |
| EXAMPLE 3 | 3.38 | 1.1 | 3.71 | 2.5 | 0.90 |
| EXAMPLE 4 | 2.97 | 1.34 | 3.98 | 2.2 | 0.90 |
| EXAMPLE 5 | 2.40 | 1.45 | 3.47 | 2.7 | 0.60 |
| EXAMPLE 6 | 3.56 | 0.9 | 3.21 | 2.5 | 0.95 |

FIG. 7B

| EXAMPLES | DEPTH OF FIELD IN LONG-DISTANCE OBSERVATION FOCUS | | |
|---|---|---|---|
| | Far1 DEPTH (mm) | Far2 DEPTH (mm) | COMBINED Far DEPTH (mm) |
| EXAMPLE 1 | NEAR POINT:5.74 (MTF:10.00%) FAR POINT:10.47 (MTF:10.00%) BST 7.5mm | NEAR POINT:10.41 (MTF:10.00%) FAR POINT:126.39 (MTF:10.00%) BST 20mm | 5.74~ 126.39 |
| EXAMPLE 2 | NEAR POINT:6.21 (MTF:10.03%) FAR POINT:11.92 (MTF:10.05%) BST 8.5mm | NEAR POINT:11.4 (MTF:10.17%) FAR POINT:51.57 (MTF:10.00%) BST 20mm | 6.21~ 51.57 |
| EXAMPLE 3 | NEAR POINT:3.45 (MTF:10.04%) FAR POINT:7.27 (MTF:10.01%) BST 4.7mm | NEAR POINT:7.20 (MTF:10.02%) FAR POINT:55.58 (MTF:10.00%) BST 20mm | 3.45~ 55.58 |
| EXAMPLE 4 | NEAR POINT:8.49 (MTF:10.03%) FAR POINT:16.92 (MTF:10.00%) BST 11.3mm | NEAR POINT:16.61 (MTF:10.10%) FAR POINT:106.19 (MTF:10.00%) BST 29mm | 8.49~ 106.19 |
| EXAMPLE 5 | NEAR POINT:4.92 (MTF:10.00%) FAR POINT:9.67 (MTF:10.02%) BST 7mm | NEAR POINT:9.37 (MTF:10.04%) FAR POINT:47.17 (MTF:10.01%) BST 18mm | 4.92~ 47.17 |
| EXAMPLE 6 | NEAR POINT:4.65 (MTF:10.02%) FAR POINT:9.06 (MTF:10.00%) BST 6.3mm | NEAR POINT:8.72 (MTF:10.01%) FAR POINT:49.31 (MTF:10.00%) BST 15mm | 4.65~ 49.31 |

FIG. 7C

| EXAMPLES | DEPTH OF FIELD IN SHORT-DISTANCE OBSERVATION FOCUS | | | near DEPTH WIDTH |
|---|---|---|---|---|
| | near1 DEPTH (mm) | near2 DEPTH (mm) | COMBINED near DEPTH (mm) | |
| EXAMPLE 1 | NEAR POIN:2.88 (MTF:10.00%) FAR POINT:4.41 (MTF:10.01%) BST 3.5mm | NEAR POIN:4.04 (MTF:10.00%) FAR POINT:7.99 (MTF:10.01%) BST 5.6mm | 2.88~ 7.99 | 5.11 |
| EXAMPLE 2 | NEAR POIN:3.28 (MTF:10.04%) FAR POINT:4.75 (MTF:10.12%) BST 4mm | NEAR POIN:4.64 (MTF:10.06%) FAR POINT:7.56 (MTF:10.02%) BST 6mm | 3.28~ 7.56 | 4.28 |
| EXAMPLE 3 | NEAR POIN:1.63 (MTF:10.42%) FAR POINT:2.60 (MTF:10.09%) BST 2mm | NEAR POIN:2.60 (MTF:10.02%) FAR POINT:4.76 (MTF:10.03%) BST 3.37mm | 1.63~ 4.76 | 3.13 |
| EXAMPLE 4 | NEAR POIN:2.25 (MTF:10.20%) FAR POINT:3.06 (MTF:10.15%) BST 2.6mm | NEAR POIN:3.05 (MTF:10.01%) FAR POINT:4.31 (MTF:10.12%) BST 3.6mm | 2.25~ 4.31 | 2.06 |
| EXAMPLE 5 | NEAR POIN:2.31 (MTF:10.39%) FAR POINT:3.37 (MTF:10.17%) BST 2.87mm | NEAR POIN:3.30 (MTF:10.19%) FAR POINT:5.31 (MTF:10.18%) BST 4.5mm | 2.31~ 5.31 | 3.00 |
| EXAMPLE 6 | NEAR POIN:2.46 (MTF:10.02%) FAR POINT:3.46 (MTF:10.07%) BST 2.96mm | :3.46 (MTF:10.02%) FAR POINT:5.46 (MTF:10.03%) BST 4.4mm | 2.46~ 5.46 | 3.00 |

ENDOSCOPE SYSTEM

TECHNICAL FIELD

The present invention relates to an endoscope system, and particularly, to a depth-of-field endoscope system.

BACKGROUND ART

It is generally known that the depth of field narrows down with an increase in the number of pixels of an imaging element in a device including the imaging element such as an endoscope system. More specifically, if the pixel pitch (horizontal and vertical dimension of one pixel) is reduced to increase the number of pixels in the imaging element, the permissible circle of confusion is also reduced accordingly, and the depth of field of the imaging apparatus narrows down. To expand the depth of field, for example, Patent Literature 1 is disclosed, wherein an optical path division means divides a subject image into two images with different focuses. Different imaging elements form the images, and the two images are combined to acquire an image with an expanded depth of field.

On the other hand, an aperture value of an optical system can be increased to maintain the depth of field. However, there are problems that the image quality is degraded by an increase in noise and that the resolving power is decreased by an increase in the influence of diffraction. An example of a technique for improving the resolving power is disclosed in Patent Literature 2, wherein one imaging element forms two subject images with different focuses divided by an optical path division element, and the two images are added to acquire a combined image with improved resolving power.

CITATION LIST

Patent Literature

{PTL 1}
Japanese Unexamined Patent Application, Publication No. 2003-078802
{PTL 2}
Japanese Unexamined Patent Application, Publication No. 2004-313523

SUMMARY OF THE INVENTION

Technical Problem

However, in the technique of Patent Literature 1, a plurality of imaging elements are provided to form subject images with different focuses. Therefore, the imaging apparatus is enlarged, or the manufacturing cost is increased. In the technique of Patent Literature 2, although the expansion of the dynamic range and the improvement of the resolving power can be realized, the difference in focus between the two subject images is too large. Therefore, an unfocused area is generated between the depths of field, or the depth of field cannot be expanded because of excessive overlapping of the depths.

The present invention has been made in view of the circumstances, and an object of the present invention is to provide an endoscope system that can reduce the manufacturing cost and acquire an image with an expanded depth of field, without enlarging the apparatus.

Solution to Problem

To attain the object, the present invention provides the following means.

An aspect of the present invention provides an endoscope system including: an objective optical system that is provided at an insertion portion tip and that acquires a subject image; an optical path division means for dividing the subject image into two optical images with different focuses; an imaging element that forms the two optical images with different focuses at the same time to acquire two images; an image correction means for correcting the two images acquired by the imaging element so that differences other than the focuses become substantially the same; and an image combination processing unit that selects an image with a relatively high contrast in predetermined corresponding areas between the two images corrected by the image correction means to generate a combined image.

BRIEF DESCRIPTION OF DRAWINGS

FIG. 7A is a chart of numeric data of the depth of field and the like in the endoscope system according to Examples of the present invention.

FIG. 7B is a chart of numeric data of the depth of field and the like in the endoscope system according to Examples of the present invention.

FIG. 7C is a chart of numeric data of the depth of field and the like in the endoscope system according to Examples of the present invention.

DESCRIPTION OF EMBODIMENTS

Hereinafter, an embodiment of the present invention will be described with reference to the drawings.

First Embodiment

Figure 1:
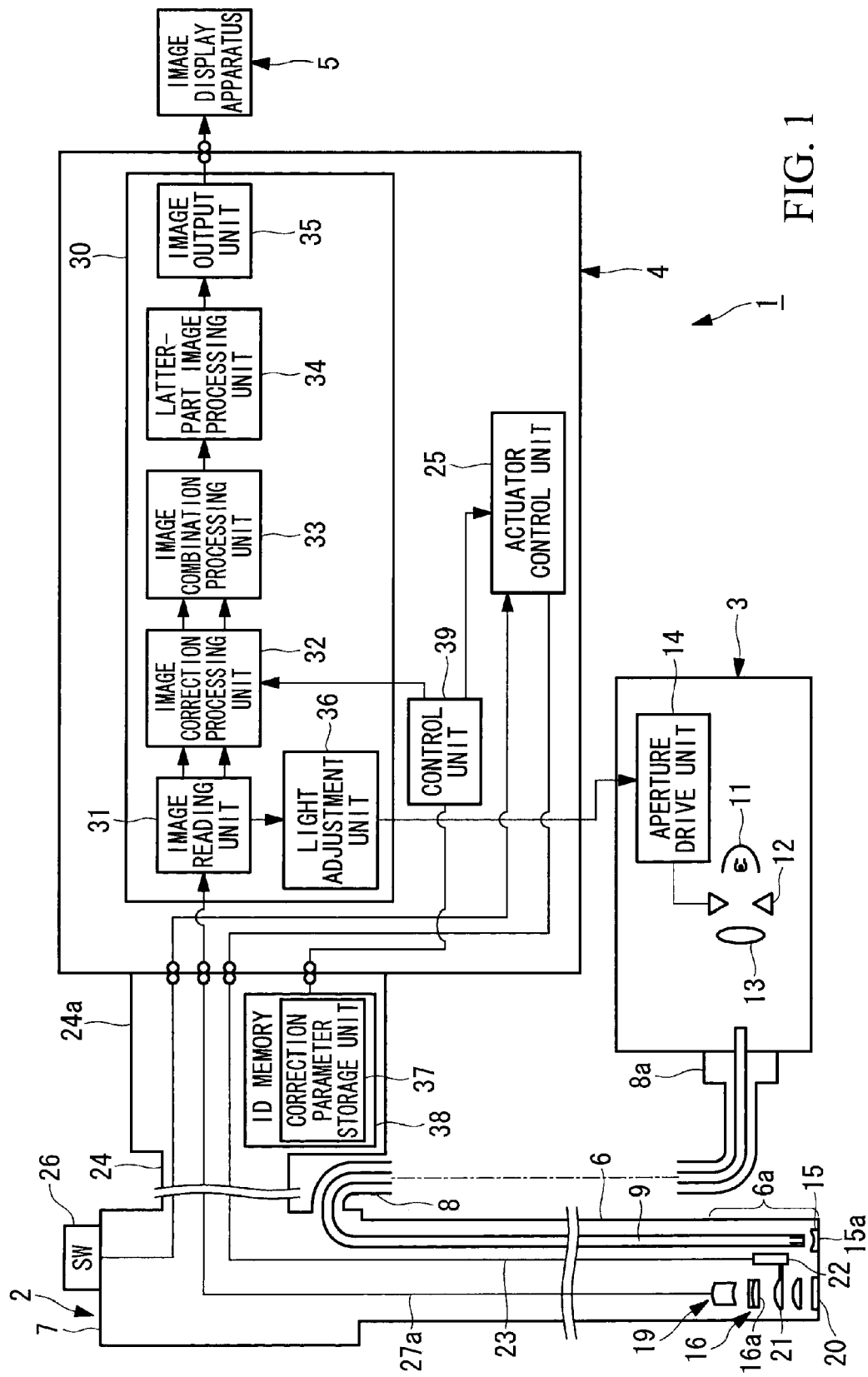
FIG. 1 is a schematic block diagram of an endoscope system according to an embodiment of the present invention.

As shown in FIG. 1, an endoscope system 1 of a first embodiment of the present invention includes: an endoscope 2 inserted to a subject; a light source apparatus 3 that supplies illumination light to the endoscope 2; a processor apparatus 4 that applies image processing to an image signal acquired by an imaging element provided in the endoscope 2; and an image display apparatus 5 that displays an endoscope image of an image signal subjected to predetermined image processing by the processor apparatus 4.

The endoscope 2 includes: an elongated insertion portion 6 inserted to the subject; an operation unit 7 provided at a back end of the insertion portion 6; and a first cable 8 extended from the operation unit 7, and a light guide 9 that transmits the illumination light is inserted to the first cable 8. A tip portion 6a of the insertion portion 6 of the endoscope 2 is provided with: an illumination lens 15 that diffuses the illumination light emitted from the light guide 9; an objective optical system 16 that acquires a subject image; and an imaging unit 19 that images a subject image. A light guide connector 8a at an edge of the first cable 8 is removably connected to the light source apparatus 3 so that a back end portion of the light guide 9 inserted to the first cable 8 serves as an incident end of the illumination light.

The light source apparatus 3 includes a lamp 11, such as a xenon lamp, as a light source. The light source is not limited to the lamp 11 such as a xenon lamp, and a light-emitting diode (abbreviated as LED) may be used. An aperture 12 adjusts a passing light amount of white light generated by the lamp 11. A condenser lens 13 collects the light, and the light enters (supplied to) an incident end surface of the light guide 9. An aperture drive unit 14 can change the amount of opening of the aperture 12.

The light guide 9 guides the illumination light entered in the incident end (back end side) from the light source apparatus 3, toward the tip portion 6a of the insertion portion 6. The illumination lens 15 arranged on a front end surface of the tip portion 6a diffuses the illumination light guided to the tip portion 6a, from an emission end (front end side) of the light guide 9. The light is emitted through an illumination window 15a to illuminate a part to be observed in the subject.

The objective optical system 16 attached to an observation window 20 provided adjacent to the illumination window 15a of the tip portion 6a forms, on an imaging element 17 arranged behind the objective optical system 16, a subject image of the illuminated part to be observed.

The objective optical system 16 includes: an optical element group 16a including a plurality of optical elements; a focus lens 21 as a focal point switch mechanism that selectively adjusts the focus or focal point to two observation areas for long-distance observation and short-distance observation; and an actuator 22 that drives the focus lens 21.

The imaging unit 19 includes: a polarization beam splitter 18 that is provided closer to the back end portion of the insertion portion 6 of the objective optical system 16 and that divides the subject image into two optical images with different focuses; and the imaging element 17 that forms two optical images to acquire two images.

Figure 2:
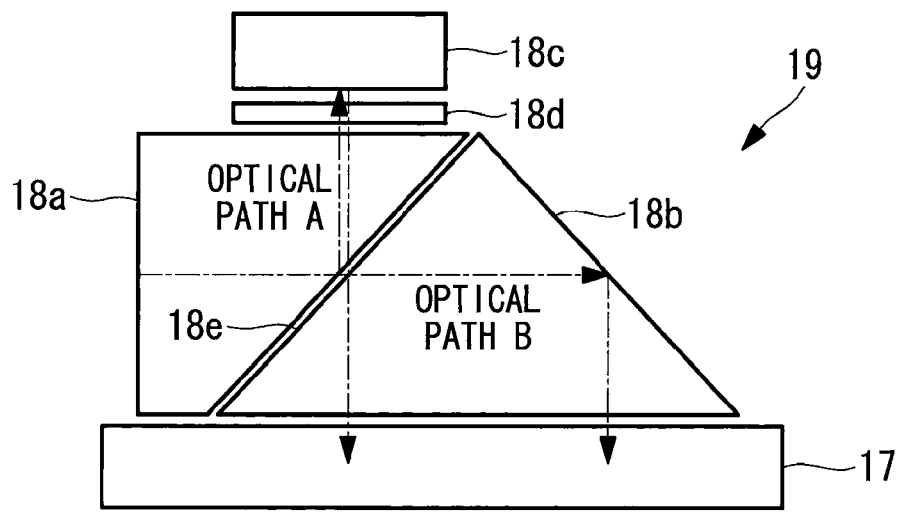
FIG. 2 is a schematic block diagram of an imaging element applied to the endoscope system according to the embodiment of the present invention.

As shown in FIG. 2, the polarization beam splitter 18 includes a first prism 18a, a second prism 18b, a mirror 18c, and a λ/4 plate 18d. Each of the first prism 18a and the second prism 18b includes a beam split surface at 45 degrees to the optical axis, and a polarization separation film 18e is provided on the beam split surface of the first prism 18a. The beam split surfaces of the first prism 18a and the second prism 18b are abutted to each other through the polarization separation film 18e to form the polarization beam splitter 18. The mirror 18c is provided near the end surface of the first prism 18a through the λ/4 plate 18d, and the imaging element 17 is attached to the end surface of the second prism 18b.

The polarization separation film 18e provided on the beam split surface of the first prism 18a separates the subject image from the objective optical system 16 into P components (transmitted light) and S components (reflected light), and the subject image is separated into two optical images: an optical image on the reflected light side; and an optical image on the transmitted light side.

The polarization separation film 18e reflects the optical image of the S components to the opposite side of the imaging element 17, and the optical image passes through an A optical path and transmits through the λ/4 plate 18d. The mirror 18c returns the optical image toward the imaging element 17. The returned optical image transmits through the λ/4 plate 18d again, and the polarization direction is rotated 90°. The optical image transmits through the polarization separation film 18e, and the imaging element 17 forms the optical image.

The optical image of the P components transmits through the polarization separation film 18e and passes through a B optical path. A mirror surface that is provided on the opposite side of the beam split surface of the second prism 18b and that perpendicularly returns the optical light toward the imaging element 17 reflects the optical image, and the imaging element 17 forms the optical image. In this case, prism glass paths are set to generate a predetermined optical path difference of about, for example, several μm between the A optical path and the B optical path, and two optical images with different focuses are formed on the light receiving surface of the imaging element 17.

More specifically, the first prism 18a and the second prism 18b are arranged so that the optical path length on the reflected light side is shorter (smaller) than the optical path length (glass path length) on the transmitted light side leading to the imaging element 17 in the first prism 18a, in order to allow separating the subject image into two optical images with different focus positions.

Figure 3:
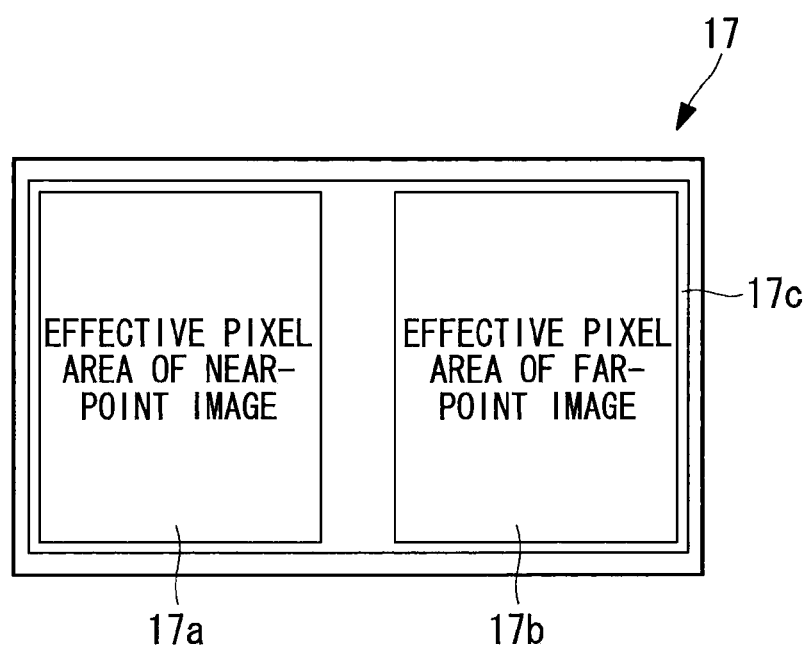
FIG. 3 is a schematic block diagram of an imaging element applied to the endoscope system according to the embodiment of the present invention.

As shown in FIG. 3, the imaging element 17 includes two light receiving areas (effective pixel areas) 17a and 17b in the entire pixel area of the imaging element 17, in order to individually receive and form two optical images with different focus positions. To form two optical images, the light receiving areas 17a and 17b are arranged to coincide with image formation surfaces of the optical images. In the imaging element 17, the focus position of the light receiving area 17a is shifted (deviated) toward the near point relative to the light receiving area 17b, and the focus position of the light receiving area 17b is shifted toward the far point relative to the light receiving area 17a. In this way, two optical images with different focuses are formed on the light receiving surface of the imaging element 17.

The first prism 18a and the second prism 18b may have different refractive indexes to change the optical path lengths to the imaging element 17 to deviate the focus positions relative to the light receiving areas 17a and 17b.

A correction pixel area 17c for correcting geometric deviation of the two divided optical images is provided around the light receiving areas 17a and 17b. Errors in manufacturing are reduced in the correction pixel area 17c, and an image correction processing unit 32 described later corrects the images by image processing. In this way, the geometrical deviation of the optical images is eliminated.

The focus lens 21 can be moved to two positions in the direction of the optical axis, and the actuator 22 drives and moves the focus lens 21 from one of the two positions to the other position and from the other position to the one of the positions. In a state in which the focus lens 21 is set at a position on the front side (object side), the focus lens 21 is set to focus a subject in an observation area for long-distance observation. In a state in which the focus lens 21 is set at a position on the back side, the focus lens 21 is set to focus a subject in an observation area for short-distance observation.

The actuator 22 is connected to a signal line 23 inserted to the insertion portion 6, and the signal line 23 is further inserted to the second cable 24 extended from the operation unit 7. A signal connector 24a at an edge of the second cable 24 is removably connected to the processor apparatus 4, and the signal line 23 is connected to an actuator control unit 25 provided in the processor apparatus 4.

A switching operation signal from a switching operation switch 26 provided on the operation unit 7 of the endoscope 2 is also input to the actuator control unit 25, for example. The actuator control unit 25 applies a drive signal for electrically driving the actuator 22 according to the operation of the switching operation switch 26 to move the focus lens 21.

The switching operation means for generating the switching operation signal is not limited to the switching operation switch 26, but may be a switching operation lever or the like. The focus lens 21, the actuator 22, and the actuator control unit 25 form a focal point switch mechanism. The focus means in the present application is not limited to the means for moving the focus lens in the optical axis direction. For example, a means for switching the focus by inserting and removing a lens or a filter to and from the objective optical system can be used.

The imaging element 17 is connected to signal lines 27a and 27b inserted to the insertion portion 6, the operation unit 7, and the second cable 24, and the signal connector 24a is connected to the processor apparatus 4. In this way, the imaging element 17 is connected to an image processor 30 as an image processing unit provided in the processor apparatus 4.

The image processor 30 includes: an image reading unit 31 that reads images regarding the two optical images with different focus positions formed by the imaging element 17; an image correction processing unit 32 that corrects the two images read by the image reading unit 31; and an image combination processing unit 33 that executes an image combining process of combining the two corrected images.

The image correction processing unit 32 corrects the images regarding the two optical images formed in the light receiving areas 17a and 17b of the imaging element 17 so that the differences other than the focuses become substantially the same. More specifically, the image correction processing unit 32 corrects the two images so that the relative positions, angles, and magnifications in the optical images of the two images become substantially the same.

When a subject image is divided into two to form the images in the imaging element 17, there may be geometric differences. More specifically, magnification deviation, positional deviation, deviation in angle or rotation direction, and the like may be relatively generated between the optical images formed in the light receiving areas 17a and 17b of the imaging element 17. It is difficult to completely eliminate the differences in manufacturing or the like. If the amount of deviation is large, the combined image may be a double image, or unnatural unevenness of brightness may occur. Therefore, the image correction processing unit 32 corrects the geometric differences and the brightness differences.

When the difference in brightness between the two images is corrected, it is desirable to correct the difference based on a picture or an image with lower luminance between the two pictures or images or based on one of the two pictures or images with lower luminance at relatively the same position.

More specifically, the brightness is corrected according to the brighter one, that is, the one with lower strength (signal level) of a luminance signal (for example, G signal). Contrary to this correction, if the brightness is corrected according to the brighter one, the noise components included in the image also need to be amplified, and the S/N is degraded in the combined image.

In this way, the brightness is corrected based on the one with lower luminance, and the gain of the one with higher luminance is reduced (or attenuated) according to the luminance of the one with lower luminance that serves as a standard. This prevents the reduction in the image quality of the combined image caused by the degradation of the S/N.

The image combination processing unit 33 generates a combined image by selecting an image with a higher contrast in predetermined corresponding areas between the two images corrected by the image correction processing unit 32. More specifically, the contrasts in spatially the same pixel areas in the two images are compared, and the pixel area of the one with a higher contrast is selected to generate a combined image as an image obtained by combining the two images. If the contrast difference between the same pixel areas of the two images is small or substantially the same, the combined image is generated by combination image processing of adding a predetermined weight to the pixel area.

The image processor 30 further includes: a latter-part image processing unit 34 that applies latter-part image processing, such as color matrix processing, edge enhancement, and gamma correction, to the image combined by the image combination processing unit 33; and an image output unit 35 that outputs the image subjected to the latter-part image processing. The image output from the image output unit 35 is output to the image display apparatus 5.

The image processor 30 further includes a light adjustment unit 36 that generates a light adjustment signal for adjusting the image read by the image reading unit 31 to reference brightness, and the light adjustment signal generated by the light adjustment unit 36 is output to the aperture drive unit 14 of the light source apparatus 3. According to the light adjustment signal, the aperture drive unit 14 adjusts the amount of opening of the aperture 12 to maintain the reference brightness.

A correction parameter storage unit 37 storing correction parameters (information thereof) used by the image correction processing unit 32 to correct the image is also provided in the present embodiment.

The endoscope 2 includes an ID memory 38 storing endoscope identification information (endoscope ID) unique to the endoscope 2, and the correction parameter storage unit 37 storing correction parameters corresponding to the endoscope 2 is provided if there are unique correction parameters to be corrected in the endoscope 2.

The images regarding the two optical images may have the geometrical difference, brightness difference, or color difference due to shading characteristics of the optical path division element or the imaging element or due to wavelength characteristics of the λ/4 plate, for example. If there is a difference between two images, unnatural brightness unevenness or color unevenness may occur in the combined image. To correct this, the correction parameters are determined in consideration of the characteristics of the optical path division element, the imaging element, and the λ/4 plate.

The image correction processing unit may perform the correction by receiving preset correction parameters from a correction parameter unit. For example, the amount of deviation can be set in advance in the correction parameter unit at the factory shipment. When the endoscope is connected to the image processor, the connection of the endoscope can be recognized, and corresponding parameters can be invoked from the correction parameter unit to perform the correction.

If there is no unique correction parameter to be corrected, the correction parameter storage unit 37 does not have to be provided. Although the correction parameter storage unit 37 is provided inside of the ID memory 38, the arrangement is not limited to this. The correction parameter storage unit 37 may be provided in a memory separate from the ID memory 38.

The control unit 39 of the image processor 30 identifies whether there is a correction, based on the endoscope ID provided in the endoscope 2. If there is a correction, the control unit 39 reads the correction parameters from the correction parameter storage unit 37 in the ID memory 38 stored in the endoscope 2 and sends the correction parameters to the image correction processing unit 32.

The image correction processing unit 32 performs image correction corresponding to the imaging unit 19 mounted on the endoscope 2 based on the correction parameters transferred from the control unit 39.

The image correction processing unit 32 uses the correction parameters and sets one of the two pictures or images as a reference picture or a reference image to perform the image correction, such as correction of difference in magnification and correction of difference in position. For example, the magnification deviation may occur between two images due to the specifications of the objective optical system 16.

To make the size of the objective optical system 16 relatively small, the telecentricity may be broken, and the light beam may be designed to obliquely enter the imaging element 17. For example, a negative incident angle is designed, wherein an angle formed with the optical axis is the incident angle, the clockwise direction is positive, and the counterclockwise direction is negative.

If the focus position is deviated in the objective optical system with the broken telecentricity, magnification deviation may occur between two images.

Under the designed specifications, the amount of deviation is stored in advance in the correction parameter storage unit 37. When the target endoscope 2 is connected to the processor apparatus 4, the endoscope 2 is recognized, and corresponding parameters are invoked from the correction parameter storage unit 37 to perform the correction.

The relative positions of the pixels of two images may be minutely deviated in the assembly of the imaging unit 19. In this case, the amount of deviation at manufacturing is stored in the correction parameter storage unit 37, and the image correction processing unit 32 corrects the deviation. In the correction of the deviation of the position, a process of modifying the reading positions of the two images is executed so that the relative positions of the image formed in the light receiving area 17a and the image formed in the light receiving area 17b of the imaging element 17 match, for example. After the positional deviation is corrected, the images are output to the image combination processing unit 33.

In place of the correction based on the correction parameters set in advance in the present embodiment, the correction may be performed when the endoscope is used, based on a separately prepared adjustment reference chart. For example, the reference chart may be arranged at a desired position of the tip portion 6a of the endoscope 2, and the image correction processing unit 32 may read the deviation of two images with respect to the reference chart to correct the deviation.

The control unit 39 sends, to the actuator control unit 25, the information of the position to be driven when the position of the focus lens 21 to be driven included in the objective optical system 16 mounted on each endoscope 2 is different. The actuator control unit 25 controls the actuator 22 to appropriately drive the actuator 22 when the type of the endoscope 2 is different.

The actuator control unit 25 also controls the actuator 22 to appropriately drive the actuator 22 when the type of the endoscope 2 is different, after acquiring the ID without the involvement of the control unit 39.

Figure 4:
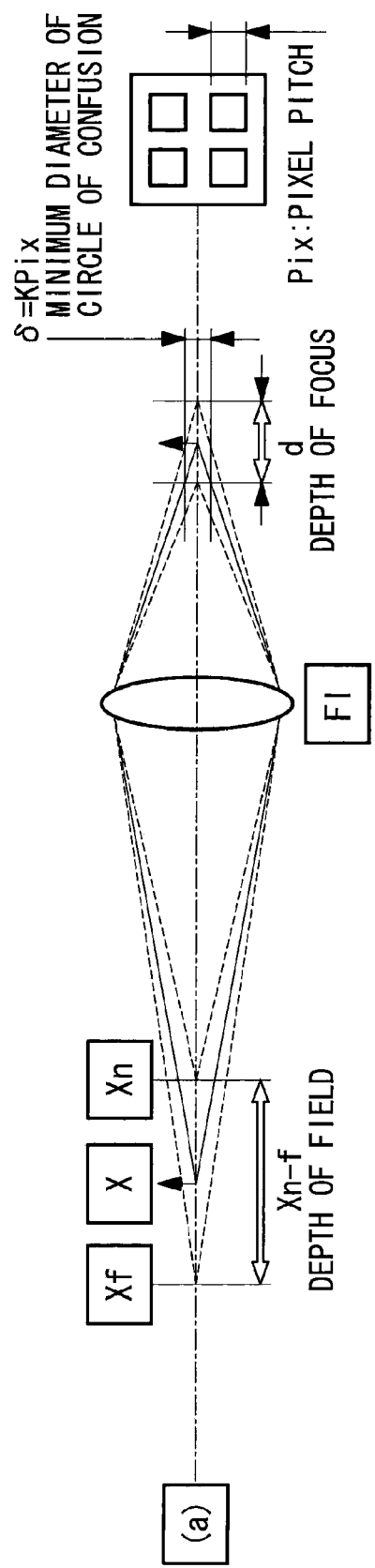
FIG. 4 is an explanatory diagram of a depth of field determined geometrically and optically.

The definition of the depth of field will be described with reference to FIG. 4 and the like. FIG. 4 is an explanatory diagram of the depth of field determined geometrically and optically.

A case of using an objective optical system (focal length Fl thereof) with a best distance X in a general endoscope and arranging an imaging element with a pixel pitch Pix shown in FIG. 3 at an image surface position X' will be considered. When an object is approximated to Xn (from X) under a condition that the imaging element is fixed, a short-distance image surface position Xn' is deviated from the imaging surface position of the imaging element.

In this case, a maximum circle of confusion that allows assuming that the object is focused is set as a permissible circle of configuration, and the circle diameter is defined as δ. If it can be recognized that the diameter of the circle of confusion on the imaging surface of the imaging element is smaller than δ, it can be assumed that the object image from X to Xn is focused.

More specifically, the range until the diameter of the circle of confusion matches δ can be defined as a depth of field on the near-point side.

The following formula is established from Newton's formula.

$$1/Xn - 1/X = \delta Fno/Fl^2 \qquad (1)$$

A case of moving the object to Xf (from X) on the far-point side can be considered to similarly define the formula of the depth of field on the far-point side as follows.

$$1/X - 1/Xf = \delta Fno/Fl^2 \qquad (2)$$

Expression (1) and Expression (2) can be combined as follows.

$$1/Xn - 1/Xf = 2\delta Fno/Fl^2 \qquad (3)$$

The depth of field corresponding to a depth of focus d is Xn−Xf.

In the formulas, X denotes the best distance, Xn denotes the distance to the near point of the depth of field, Xf denotes the distance to the far point of the depth of field, δ denotes the diameter of the permissible circle of configuration, Fl denotes the focal length of the objective optical system, and Fno denotes the effective f-number of the objective optical system.

The foregoing is the definition of a general depth of field determined geometrically and optically.

In the present embodiment, the depth of field can be expanded by the combined image compared to the depth of field determined geometrically and optically, and the depth of field can also be expanded by the combined image when the influence of diffraction cannot be ignored.

It is generally known that wave-optics influence cannot be ignored when the depth of field is defined, if the imaging element is downsized and the number of pixels is increased. This is because the geometrically and optically defined spot size is expanded at the focal position due to the influence of diffraction, and there is a deviation from the geometrical and optical calculation of the depth of field. Therefore, the diffraction is an effect that cannot be ignored in the endoscope 2 provided with a multi-pixel imaging element in which the aperture is often narrowed down to the effective f-number Fno close to the diffraction limit as in the present embodiment.

When a combined depth of field of two images with different focus positions is obtained, it is desirable that the depth ends overlap at MTF 10% or more. The following is set, wherein Fi denotes an evaluation spatial frequency on the image surface.

$$Fi = 1/k1 \cdot Pix \tag{4}$$

If defocus MTF (Modulation Transfer Function) at Fi is about 10%, a blur of image cannot be recognized by subjective evaluation, and it can be determined that the image is "viewed". In other words, the defocus position with MTF of about 10% can be assumed as the depth end.

Figure 5:
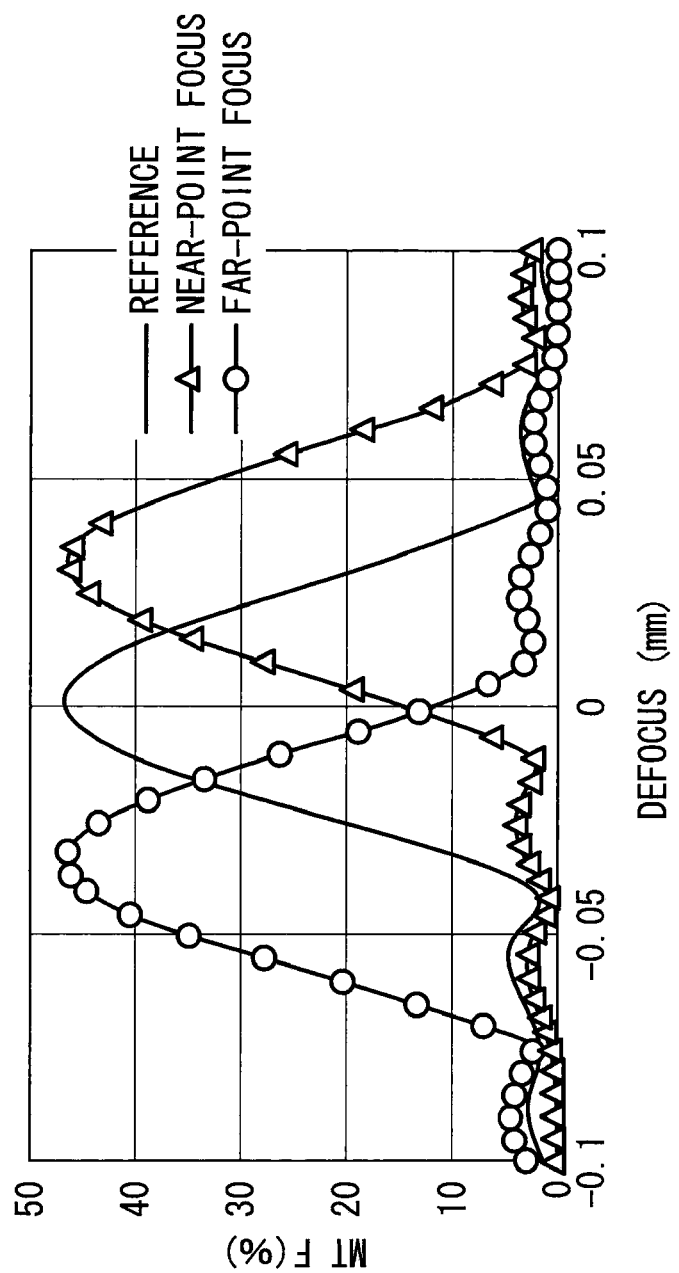
FIG. 5 is a graph showing a relationship between MTF and focus when a combined depth of field is obtained.

More specifically, when the combined depth of field of two focus states is obtained, the condition that maximizes the depth range is that the images are combined while maintaining the MTF of about 10% or greater at the depth ends (see FIG. 5). If two images are combined at an end in which the MTF is 10% or less, a depth-of-field gap is generated, and a blurred area is generated in the combined depth.

It is desirable that the end of the combined depth of field on the long-distance observation side and the end of the combined depth of field on the short-distance observation side during two-focal-point switching overlap at MTF 10%. According to this setting, the depth-of-field gap is not generated even if the two focal points are switched. The end of the combined depth of field on the long-distance observation side and the end of the combined depth of field on the short-distance observation side during two-focal-point switching may not overlap, and the combined depth of field on the short-distance observation side may be about 3 mm.

Instead of unreasonably setting a continuous depth of field, magnification observation at a closer range is made possible to improve the endoscope diagnosability. However, it is desirable that there is almost no change in the viewing angle during two-focal-point switching in focusing and that the depth width of about 3 mm is secured in consideration of the operability of the endoscope. If the viewing angle is changed during the two-focal-point switching, a variable power optical system may be used, wherein the observation magnification increases with a decrease in the distance.

In the present embodiment, the polarization beam splitter 18 that separates the subject image into two optical images is arranged to form a near-point image and a far-point image on the imaging element 17. As described, the near-point glass path and the far-point glass path of the optical images to the imaging element 17 are different based on the polarization beam splitter 18, and images with relatively different focus positions can be obtained.

Figure 6:
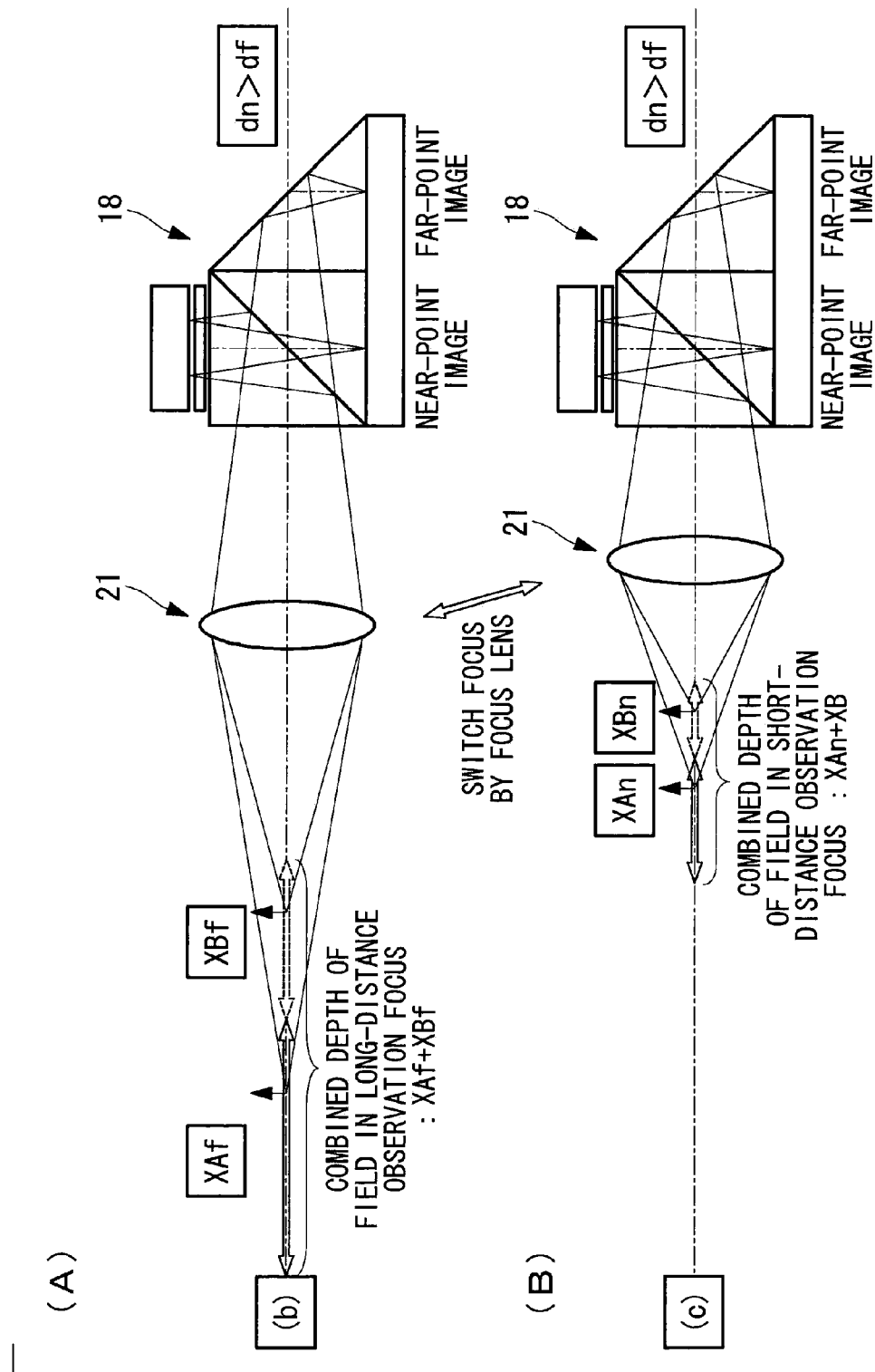
FIG. 6(A) is an explanatory diagram showing a long-distance observation focus state as a whole by focusing in an objective optical system 16.
FIG. 6(B) is an explanatory diagram showing a short-distance observation focus state as a whole by focusing in the objective optical system.

FIG. 6(A) shows a long-distance observation focus state as a whole by focusing in the objective optical system 16, and FIG. 6(B) shows a short-distance observation focus state as a whole by focusing in the objective optical system 16.

For example, as shown in FIGS. 6(A) and 6(B), when a near-point image is formed closer to the objective optical system 16 on the imaging element 17 and a far-point image is formed closer to the endoscope 2, dn>df holds true, wherein dn and df denote glass paths of the polarization beam splitter 18 to the imaging element 17.

The first prism 18a and the second prism 18b may be formed by different glasses according to the near-point optical path and the far-point optical path to the imaging element 17 to set different refractive indexes to relatively deviate the focus positions.

As a result, images regarding two optical images with different focuses can be acquired, and the image combination processing unit 33 can combine the images to obtain a combined depth of field XAf+XBf. The long-distance observation is suitable for overviewing and screening a wide range by endoscopy, and the short-distance observation is suitable to observe or diagnose details of pathology.

According to the configuration, even if an imaging element with more pixels is used, the depth of field can be expanded without reducing the resolving power. Since the focusing mechanism is included, the observation range can be freely switched to perform endoscopic observation and diagnosis with high image quality.

The imaging unit 19 of the present embodiment is set to satisfy the following condition.

$$2.4 \leq Fno/Pix \leq 4.28 \tag{5}$$

In this way, an image with an expanded depth of field can be acquired while maintaining the desired brightness and resolving power. The condition of Expression (5) is based on the following reason.

In the lens included in the objective optical system 16, it is known that the light is influenced by diffraction when an image is formed. With an increase in the effective f-number Fno of the objective optical system 16, the point image becomes large due to the influence of diffraction. If the size of the point image exceeds a limit, details of the subject look blurred even if the subject is focused.

Based on Rayleigh, the limit is defined as a limit distance that allows identifying two point images as separate images when the two images are close to each other. The limit is expressed by $1.22 \cdot \lambda \cdot Fno$, wherein $\lambda$ denotes the wavelength of light, and Fno denotes the effective f-number. The distance of the separation limit of the two point images, that is, resolving power R, is as follows.

$$R = 1.22 \cdot \lambda \cdot Fno \tag{6}$$

Meanwhile, the limit resolving power is determined by sampling theory when a charge-coupled device (abbreviated as CCD) or a CMOS sensor is used as the imaging element to form an image. The following is set, wherein Pix denotes the pixel size of the imaging element in the vertical direction.

$$R = 2 \cdot Pix \tag{7}$$

In reality, there is an influence of an interpolation method or characteristics of an electrical system in the adopted imaging system. Therefore, an arbitrary coefficient k1 is used to express the resolving power R as follows.

$$R = k1 \cdot Pix \tag{8}$$

Since the performance of the imaging element needs to be brought out sufficiently, the coefficient k1 is generally about $2 \leq k1 \leq 3$.

The following is set based on Expressions (6) and (8).

$$k1 \cdot Pix = 1.22 \cdot \lambda \cdot Fno \tag{9}$$

The effective f-number Fno set in the objective optical system 16 needs to have some margin to sufficiently attain the optical performance in consideration of production variations and the like. Therefore, the effective f-number Fno defined by the Rayleigh limit expression is actually set in consideration of an arbitrary margin coefficient k2 as follows.

$$k1 \cdot Pix = 1.22 \cdot \lambda \cdot Fno \cdot k2 \tag{10}$$

A proper range of the margin coefficient k2 is about 0.6≤k2≤1, in consideration of balance with the size and the depth of field of the objective optical system 16.

However, when the expansion of the depth of field is prioritized by permitting some degradation in the resolving power, the margin coefficient k2 may be set to about k2≤1.2.

The effective f-number Fno of the objective optical system 16 to be set is as follows based on Expressions (9) and (10).

$$\text{Fno} \cdot k2 = (1/1.22 \cdot \lambda) \cdot \text{Pix} \cdot k1 \quad (11)$$

If Expression (11) is illustrated by a relationship between the effective f-number Fno and the pixel size Pix, the following Expression (12) can be illustrated.

$$\text{Fno/Pix} = (1/1.22 \cdot \lambda) \cdot k1 \cdot k2 \quad (12)$$

It is desirable to satisfy the relationship of Expression (5) in the endoscope system using a high-pixel imaging element.

If the relationship is smaller than 2.4 that is the lower limit of the range of Expression (5), the effective f-number Fno of the objective optical system 16 is too small, and a desired depth of field cannot be obtained. Or, the depth of field is sufficient, but the Pix size of the imager is large, and the resolving power is low. Or, the resolving power is improved by increasing the number of pixels, but the imager size is large. Therefore, the objective optical system 16 is enlarged, and the diameter becomes large (insertion property is reduced) when the objective optical system 16 is mounted on the top portion 6a of the endoscope 2. This is not preferable.

On the other hand, if the relationship exceeds the upper limit of the range of Expression (5), the effective f-number Fno of the objective optical system is too large, and desired brightness cannot be obtained. At the same time, the diffraction limit is exceeded too much, or the interpolation system is not proper, and the resolving power is degraded.

In the present embodiment, an example of the imaging unit 19 satisfying the conditional expression is illustrated in the chart of FIG. 7.

FIG. 7 illustrates numeric data of Fno/Pix, Pix, Fno, k1, k2, and far1 depth (depth of field based on the light receiving area 17a in long-distance observation), far2 depth (depth of field based on the light receiving area 17b in long-distance observation), combined far depth (depth of field of the combined image in long-distance observation), near1 depth (depth of field based on the light receiving area 17a in short-distance observation), near2 depth (depth of field based on the light receiving area 17b in short-distance observation), combined near depth (depth of field (range) of the combined image in short-distance observation), near depth width (depth width from combined near depth near-point end to combined near depth far-point end), imaging system, and the number of pixels (total number of pixels of the imaging element). BST denotes the best distance as an object distance when the MTF is the maximum.

The following illustrates an outline of Examples of FIG. 7.

In Example 1, the imaging unit 19 is a complementary color synchronous system, and in this case, the coefficient k1 is about 3, and the imaging element 17 is a complementary-color solid-state imaging element with one million pixels, wherein the pixel size is 1.7 μm. The aperture of the objective optical system 16 is narrowed down to a level that does not degrade the resolving power to sufficiently secure the depth of field. More specifically, the margin coefficient k2 from the diffraction limit f-number of the objective optical system 16 is k2=0.95, and the following is set based on Expression (12).

$$\text{Fno/Pix} = 4.28 \quad (13)$$

Example 2 indicates a frame sequential system, and the coefficient k1 of about 2 can be obtained. The imaging element 17 is a monochrome imaging element with 840,000 pixels, wherein the pixel size is 1.45 μm. The brightness is prioritized in the setting of the objective optical system relative to the diffraction limit f-number. The margin coefficient k2 from the diffraction limit f-number of the objective optical system 16 is k2=0.8, and the following is set based on Expression (12).

$$\text{Fno/Pix} = 2.4 \quad (14)$$

Practically sufficient depth of field can be obtained.

In Example 3, the imaging element 17 is a synchronous imaging element of primary-color Bayer array with 84 pixels, 1.1 μm each. The diameter is relatively small (imaging size is small because of the minute pixels), and the endoscope is a high-pixel endoscope in this Example (k1=2.5). Some margin is set relative to the diffraction limit f-number, and practically necessary depth of field (k2=0.9) is maintained. More specifically, practical long-distance depth of field is maintained. In short-distance observation focusing, resolving power equivalent to that of a variable power endoscope is attained at the shortest distance, and the endoscope realizes both screening and diagnosis.

In Example 4, the imaging element 17 is a synchronous imaging element of primary-color Bayer array with 1.5 million pixels, 1.34 μm each, and the interpolation method is optimized to realize the improvement of the resolving power (k1=2.2). Some margin is set relative to the diffraction limit f-number, and practically necessary depth of field is maintained (k2=0.9). As in Example 3, the endoscope realizes both screening and diagnosis. Compared to Example 3, the long-distance observation focusing is emphasized to facilitate the screening. On the other hand, there is a depth gap between focuses, and the depth width is narrower than in Example 3 in the short-distance observation focusing. However, the advantageous effects of the present application can maintain a depth twice as much as the tele-end depth of a conventional variable power endoscope.

In Example 5, the imaging element 17 is a synchronous imaging element of primary-color Bayer array with 840,000 pixels, 1.45 μm each, and the f-number is set to prioritize the brightness in the objective optical system 16 relative to the diffraction limit f-number (k2=0.6). Practically sufficient depth of field can be obtained by the setting. The resolving power is reduced a little to a level that does not interfere the actual use, and the depth is increased for the balance in the example.

In Example 6, the imaging element 17 is a synchronous imaging element of primary-color Bayer array with 840,000 pixels, 0.9 μm each. The diameter is smaller (imaging size is small because of the minute pixels), and the endoscope is a high-pixel endoscope in this Example. The aperture is narrowed down almost to the diffraction limit f-number in a level that does not degrade the resolving power, and the depth of field is sufficiently secured. In a short-distance observation mode, resolving power equivalent to that of a variable power endoscope is attained at the shortest distance.

If an imaging system using the synchronous imaging element of primary-color Bayer array is mainly used in the implementation of the present application, Expression (5) may be as follows.

$$2.4 \leq \text{Fno/Pix} \leq 3.56 \quad (5)'$$

Figure 8:
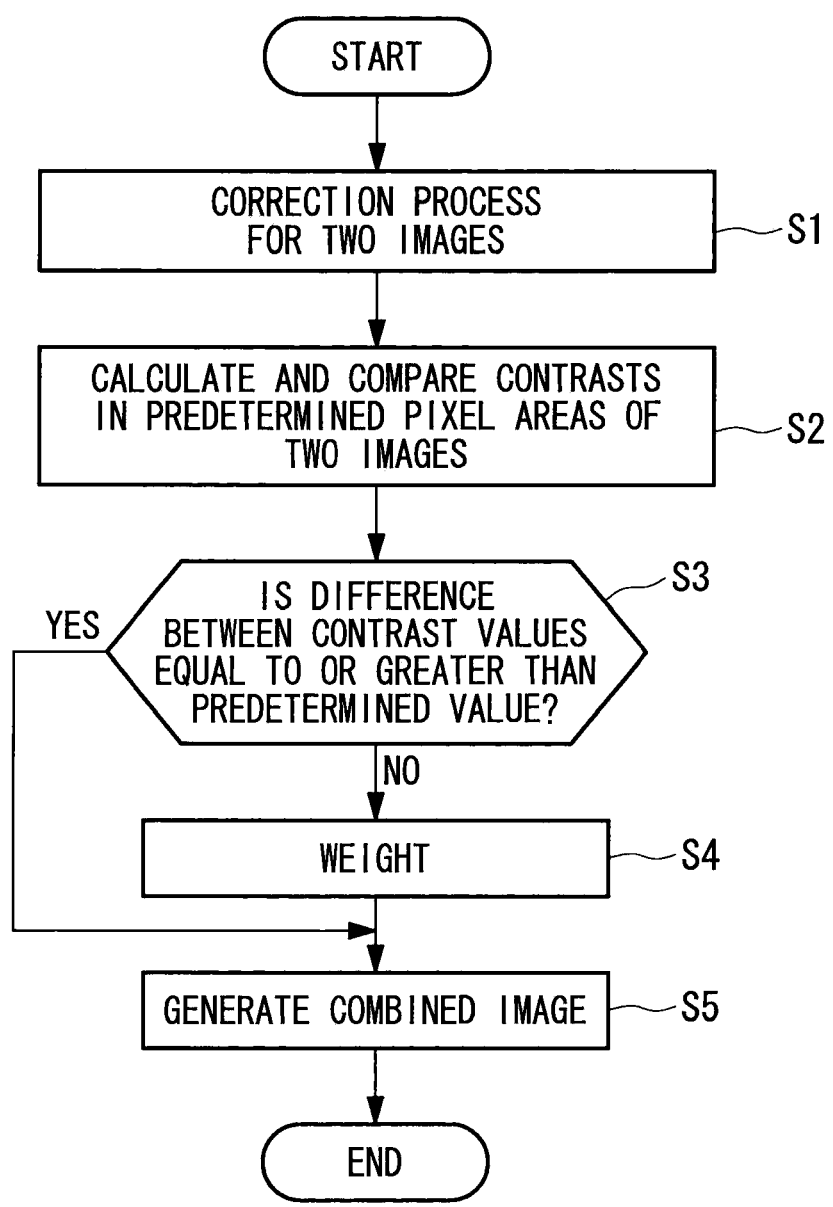
FIG. 8 is a flow chart showing a flow when two optical images are combined in the endoscope system according to the embodiment of the present invention.

A flow of combining two optical images in the present embodiment will be described with reference to a flow chart of FIG. 8.

In step S1, an image regarding the far-point image and an image regarding the near-point image with different focuses acquired by the imaging element 17 are subjected to a correction process of two far and near images by the image correction processing unit 32. More specifically, the two images are corrected according to the preset correction parameters so that the relative positions, angles, and magnifications in the optical images of two images become substantially the same, and the corrected images are output to the image combination processing unit 33. The difference in brightness or color between the two images may also be corrected if necessary.

In step S2, the image combination processing unit 33 combines the two images subjected to the correction process. In this case, contrast values are calculated and compared in corresponding pixel areas of the two far and near images. In step S3, whether there is a difference between the compared contrast values is determined. If there is a difference in the contrast, the process proceeds to step S5, and areas with high contrast values are selected and combined. If the difference between the compared contrast values is small or substantially the same, which one of the two far and near images will be selected is an unstable factor in the process. For example, if there is a fluctuation of signal, such as noise, a discontinuous area is generated in the combined image, or there is a defect that the subject image that should be resolved is blurred. Therefore, the process proceeds to step S4 to perform weighting. In step S4, if the contrast values are substantially the same between the two images in the pixel areas for which the contrast is compared, weighting is performed, and the weighted images are added in the following step S5 to eliminate the unstableness of selecting an image.

A weighting coefficient W (i, j) at coordinates (i, j) of the image is as follows, wherein R denotes a contrast ratio of two images, and A and B denote predetermined arbitrary constants.

$$W(i,j)=1 \quad A<R \tag{15}$$

$$W(i,j)=0 \quad R<B \tag{16}$$

$$W(i,j)=(R-B)/(A-B) \quad B\leq R\leq A \tag{17}$$

Figure 9:
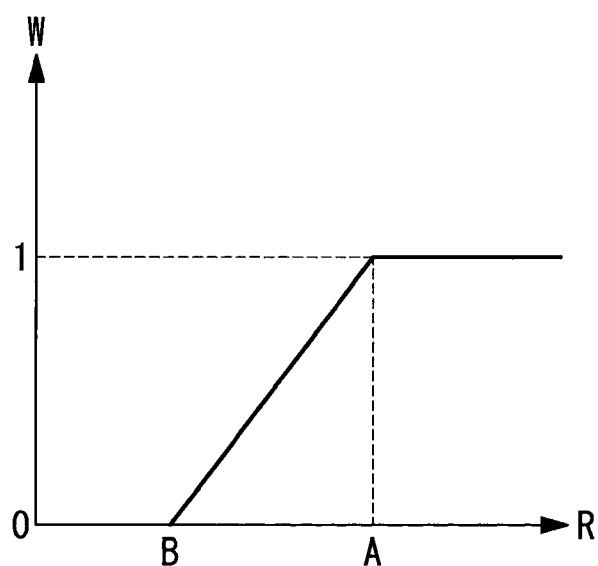
FIG. 9 is a graph showing a weighting coefficient when two images are combined in the endoscope system according to the embodiment of the present invention.

As shown in FIG. 9, Expression (15) indicates a state that one of the two images will be surely selected when the contrast ratio is greater than A, and only the far-point image is selected because W=1.

Expression (16) indicates a state that one of the two images will be surely selected when the contrast ratio is smaller than B, and only the near-point image is selected because W=0.

In Expression (17), the contrast ratios of the far and near images are substantially the same, and the area is unstable. Therefore, the weighting coefficient W is applied in a line shape in the area, and the far-point image (Rf, Gf, Bf) and the near-point image (Rn, Gn, Bn) are added at a certain ratio. The combined image becomes discontinuous without this process.

Therefore, combined signals R', G', and B' are as follows, wherein RGB signals of two images are Rf, Gf, Bf, Rn, Gn, and Bn.

$$G'=W(i,j)Gf(i,j)+(1-W(i,j))Gn(i,j) \tag{18}$$

$$R'=W(i,j)Rf(i,j)+(1-W(i,j))Rn(i,j) \tag{19}$$

$$B'=W(i,j)Bf(i,j)+(1-W(i,j))Bn(i,j) \tag{20}$$

The image combination processing unit 33 combines the two images corrected by the image correction processing unit 32 to generate a combined image and outputs the combined image toward the image display apparatus 5. The image display apparatus 5 displays the combined image.

In this way, according to the present embodiment, an image with an expanded depth of field can be acquired in the short-distance observation and the long-distance observation while preventing the generation of a discontinuous area in the combined image due to noise or the like and preventing the blur of an optical image. Since the two images are formed by the same imaging element, the manufacturing cost can be smaller than in an apparatus including a plurality of imaging elements, and an image with an expanded depth of field can be acquired without enlarging the apparatus.

According to the setting satisfying Expression (5), a desired depth of field can be obtained, and the size of the apparatus can be small so that the apparatus can be mounted on the top portion 6a of the endoscope 2. Desired brightness can be secured, and the degradation of the resolving power can be prevented.

Figure 10:
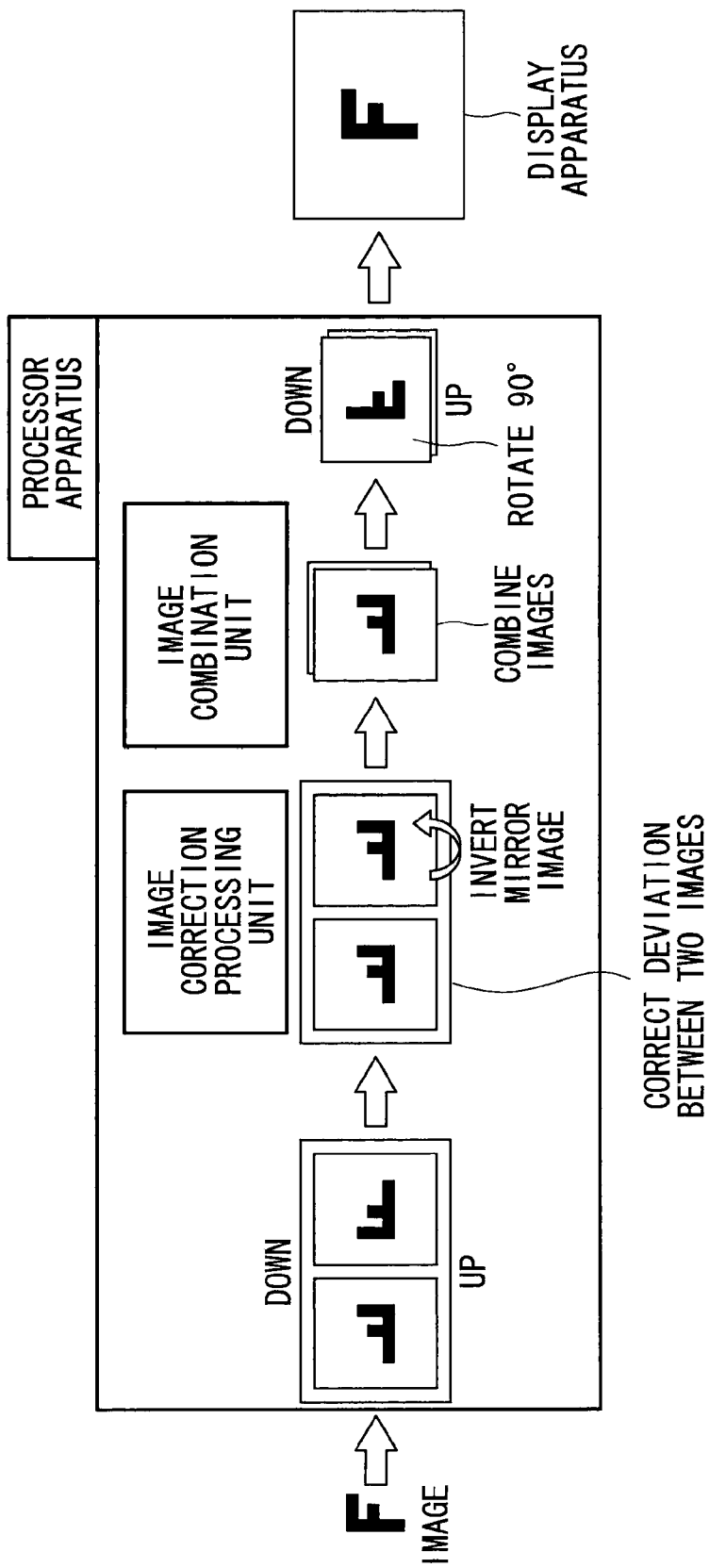
FIG. 10 is a diagram showing an image formation state when the imaging element forms an image after reflection for an odd number of times by a polarization beam splitter in the endoscope system according to the embodiment of the present invention.

In the case of the polarization beam splitter 18 of FIG. 2, the optical images are formed on the imaging element 17 after one reflection, that is, after reflection for an odd number of times. Therefore, one of the images is in an image formation state (mirror image) as shown in FIG. 10, and the processor apparatus 4 executes image processing of inverting the mirror image to match the image direction. The correction of the mirror image by optical reflection for an even number of times may enlarge the objective optical system or increase the cost of the prism. Therefore, it is preferable that the image correction processing unit 32 inverts the mirror image to correct the mirror image based on the reflection for an odd number of times.

If the imaging element has an elongated shape in the longitudinal direction of the endoscope, it is preferable to take the aspect ratio of the display apparatus into account to rotate the combined image as necessary.

When the polarization beam splitter 18 is applied for the polarization and separation as in the present embodiment, there is a difference in brightness between the separated images unless the polarization state of the separated light is circularly polarized light. More specifically, a systematic difference in brightness can be relatively easily corrected by image processing. However, when there is a local difference in brightness under an observation condition, the correction cannot be completely performed, and there is brightness unevenness in the combined image. The condition that the subject image is broken from the circularly polarized light is determined by the angle of observing the subject, for example. The angle is generally called a Brewster's angle θb, and if the angle is greater than this angle, the polarization state from the subject is broken from the circularly polarized light.

$$\theta b=\text{Arctan}(n2/n1) \tag{21}$$

Figure 11:
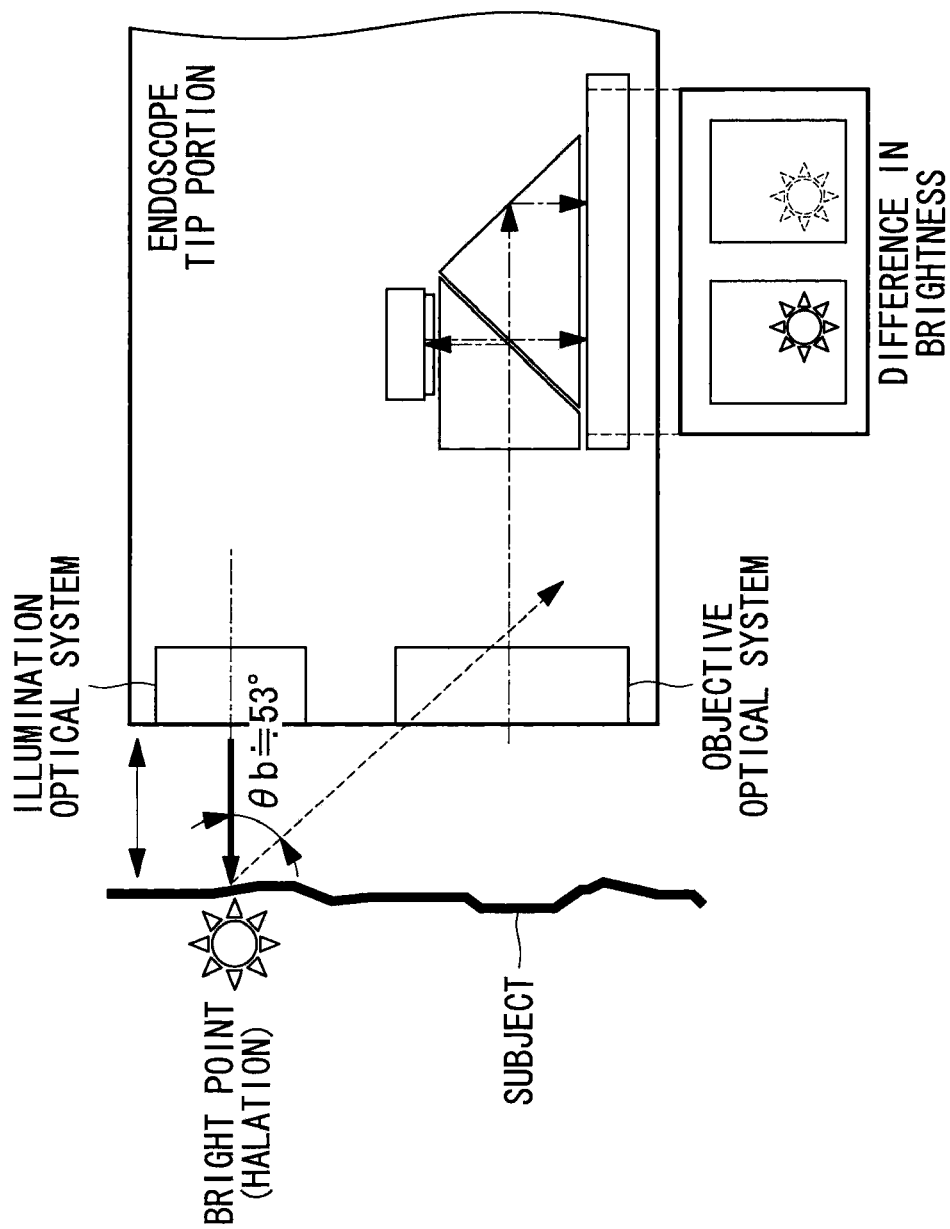
FIG. 11 is a diagram showing a relationship between a configuration of an endoscope tip and a Brewster's angle.

The subject observed by the endoscope is covered by a mucous membrane, and assuming that the refractive index of the mucous membrane is substantially the same as water (n2=1.333), θb is about 53°. For example, the following is observation of the subject when the front end of the endoscope has a configuration as shown in FIG. 11. When the Brewster's angle θb=53° is applied, the angle exceeds this angle relatively around the field of view under a relatively short-distance condition. More specifically, there is a possibility that brightness unevenness is generated relatively around the field of view of the combined image. The brightness unevenness with broken polarization state is prominent when the brightness distribution of the subject is relatively saturated.

Although it is around the field of view, the blood stream or mucous membrane structure of the subject image is often viewed relatively closely in the endoscope, and it is likely that the image is significantly troublesome for the user.

Figure 12:
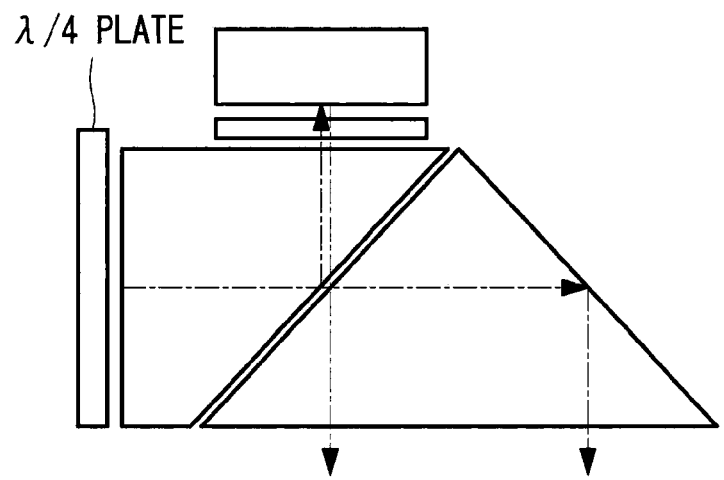
FIG. 12 is a diagram showing an example of arranging a λ/4 plate closer to an object relative to a polarization separation film of an optical path division element.
Figure 13:
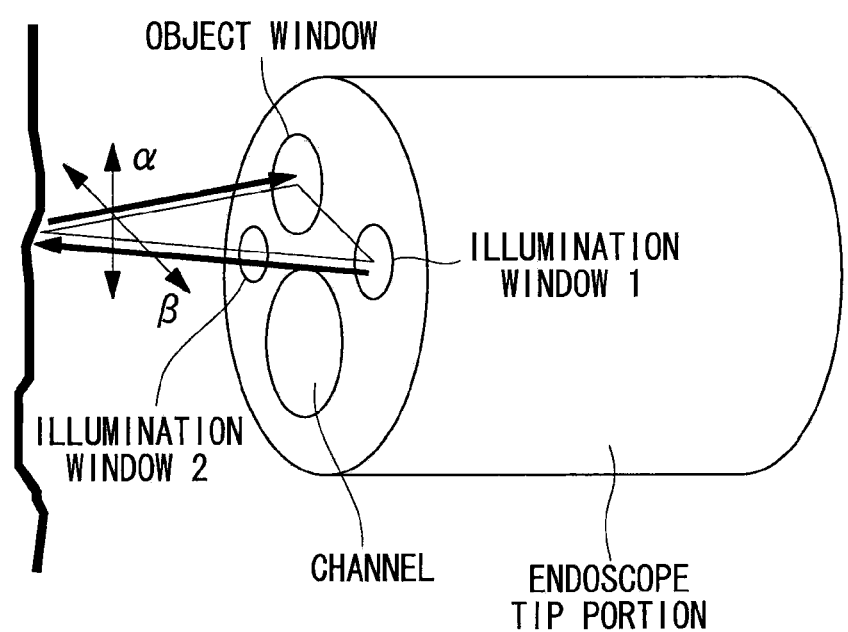
FIG. 13 is a diagram showing a positional relationship between the λ/4 plate and an illumination optical system.

Therefore, as shown for example in FIG. 12, it is preferable to arrange the λ/4 plate closer to the object relative to the polarization separation film of the optical path division element so as to restore the circularly polarized light from the state in which the polarization state is broken. To obtain the maximum elimination effect of the polarization state, it is desirable to arrange the λ/4 plate in an α or β direction as shown in FIG. 13.

More specifically, the high speed shaft of the λ/4 plate is arranged substantially parallel or perpendicular to the plane including the optical axis of the objective optical system and including the optical axis of an illumination optical system farthest from the object optical system among a plurality of illumination optical systems when the plurality of illumination optical systems are arranged at the insertion portion tip, or the high speed shaft of the λ/4 plate is arranged substantially parallel or perpendicular to the plane including the optical axis of the objective optical system and including the optical axis of an illumination optical system with the largest illumination light amount among the plurality of illumination optical systems.

Usually, the endoscope includes a plurality of illumination windows in consideration of the light distribution characteristics. It can be recognized from FIG. 11 that the Brewster's angle θb increases with an increase in the distance between the illumination window and the object window. More specifically, it is more desirable to arrange the high speed shaft of the λ/4 plate on an illumination window far from the object window. As described, the brightness unevenness is more prominent under a saturated condition, and the λ/4 plate may be arranged for an illumination window with a greater illumination light amount.

It is desirable that the λ/4 plate for eliminating the polarization and the λ/4 plate arranged on the optical path division element for polarization and separation are thin elements, such as resin films, to miniaturize the endoscope tip portion. For example, a phase difference film used for a liquid crystal monitor or a touch panel can be used to miniaturize the endoscope. Such a λ/4 resin film does not have to be arranged just before the optical path division element as described above. The λ/4 resin film can be arranged closer to the object relative to the polarization separation film, and for example, the λ/4 resin film may be attached to a plane portion such as an infrared cut filter.

A crystal filter with a crystal axis forming 45 degrees relative to the incident surface as seen from the object side of the polarization beam splitter 18 may be arranged on the object side of the polarization beam splitter 18 to eliminate the difference in brightness between the two separated images.

REFERENCE SIGNS LIST

1 endoscope system
2 endoscope
3 light source apparatus
4 processor apparatus
5 image display apparatus
6 insertion portion
16 objective optical system
17 imaging element
17a, 17b light receiving areas
17c correction pixel area
18 polarization beam splitter
18a first prism
18b second prism
18c mirror
18d λ/4 plate
18e polarization separation film
19 imaging unit
30 image processing unit
32 image correction processing unit
33 image combination processing unit

The invention claimed is:
1. An endoscope system comprising:
   an objective optical system that is provided at an insertion portion tip and that acquires a subject image;
   an optical path division means for dividing the subject image into two optical images with different focuses;
   an imaging element that forms the two optical images with different focuses at the same time to acquire two images;
   an image correction means for correcting the two images acquired by the imaging element so that differences other than the focuses become substantially the same; and
   an image combination processing unit that selects an image with a relatively high contrast in predetermined corresponding areas between the two images corrected by the image correction means to generate a combined image, wherein
   the optical path division means is a polarization beam splitter, and
   a crystal filter including a crystal shaft forming 45 degrees relative to an incident surface of the polarization beam splitter is arranged on an object side of the polarization beam splitter.
2. The endoscope system according to claim 1, wherein if the contrasts of the predetermined areas are substantially the same in the predetermined corresponding areas between the two images, the image combination processing unit weights the predetermined areas to generate the combined image.
3. The endoscope system according to claim 1, wherein the image correction means corrects the images so that positions, angles, and magnifications of the two optical images become substantially the same.
4. The endoscope system according to claim 1, wherein the image correction means corrects the images so that brightness and colors of the two optical images become substantially the same.
5. The endoscope system according to claim 1, wherein when a mirror image of one of the optical images divided by the optical path division means is inverted and formed on the imaging element, the image correction means inverts the mirror image of one of the two images.
6. The endoscope system according to claim 1, wherein the objective optical system and the imaging element satisfy the following condition

$$2.4 \leq Fno/Pix \leq 4.28,$$

wherein Fno denotes an effective f-number of the objective optical system, and Pix denotes a pixel size of the imaging element in a vertical direction.
7. The endoscope system according to claim 1, wherein the crystal filter is a λ/4 plate, and
   a high speed shaft of the λ/4 plate is arranged substantially parallel or perpendicular to a plane including an optical axis of an illumination optical system arranged at the insertion portion tip and including an optical axis of the objective optical system.

8. The endoscope system according to claim 7, wherein
a plurality of illumination optical systems are arranged at the insertion portion tip, and the high speed shaft of the λ/4 plate is arranged substantially parallel or perpendicular to a plane including the optical axis of the objective optical system and including an optical axis of an illumination optical system farthest from the objective optical system among the plurality of illumination optical systems.

9. The endoscope system according to claim 7, wherein
a plurality of illumination optical systems are arranged at the insertion portion tip, and the high speed shaft of the λ/4 plate is arranged substantially parallel or perpendicular to a plane including the optical axis of the objective optical system and including an optical axis of an illumination optical system with a largest illumination light amount among the plurality of illumination optical systems.

10. The endoscope system according to claim 7, wherein the λ/4 plate is polymeric film.

* * * * *